US009527999B2

(12) United States Patent
Schlumpf et al.

(10) Patent No.: US 9,527,999 B2
(45) Date of Patent: Dec. 27, 2016

(54) DIALDIMINE, EMULSION CONTAINING DIALDIMINE, AND BICOMPONENT POLYURETHANE COMPOSITION, AND THE USE THEREOF

(71) Applicant: SIKA TECHNOLOGY AG, Baar (CH)

(72) Inventors: Michael Schlumpf, Stallikon (CH); Urs Burckhardt, Zurich (CH)

(73) Assignee: SIKA TECHNOLOGY AG, Baar (CH)

( * ) Notice: Subject to any disclaimer, the term of this patent is extended or adjusted under 35 U.S.C. 154(b) by 54 days.

(21) Appl. No.: 13/727,181

(22) Filed: Dec. 26, 2012

(65) Prior Publication Data
US 2013/0130039 A1 May 23, 2013

Related U.S. Application Data

(62) Division of application No. 12/449,739, filed as application No. PCT/EP2008/052729 on Mar. 6, 2008, now abandoned.

(30) Foreign Application Priority Data

Mar. 6, 2007 (EP) .................................... 07103554

(51) Int. Cl.
*C08G 18/10* (2006.01)
*C08L 75/08* (2006.01)
(Continued)

(52) U.S. Cl.
CPC .............. *C08L 75/08* (2013.01); *C07C 275/20* (2013.01); *C08G 18/0823* (2013.01);
(Continued)

(58) Field of Classification Search
None
See application file for complete search history.

(56) References Cited

U.S. PATENT DOCUMENTS 3,165,510 A 1/1965 Hoenen et al.
4,108,842 A 8/1978 Konig et al.
(Continued)

FOREIGN PATENT DOCUMENTS

EP 1 524 282 A1 4/2005
EP 1 728 840 A1 12/2006
(Continued)

OTHER PUBLICATIONS

John. A. Nairn "Polymer Structure and Characterization" 2007, pp. 1-77.*
Abstract of Soviet Union Patent Application No. 16 459 A, filed Aug. 19, 1964.

*Primary Examiner* — Clinton Brooks
(74) *Attorney, Agent, or Firm* — Oliff PLC

(57) ABSTRACT

Dialdimines of formula (I) and emulsions and uses thereof. In particular, they can be used for the preparation of pasty curing agent or accelerator components for polymers having isocyanate groups, which lead to very high early strength, which have good flow behavior on pumping and which can be formulated without VOC solvents, in particular without N-alkylpyrrolidones. These components can be homogeneously or inhomogeneously mixed in an outstanding manner, in particular in a laminar manner, with components which contain polyurethane polymers having isocyanate groups, the two-component compositions thus obtained curing rapidly, having extremely high early strength and remaining without annoying weaknesses.

7 Claims, 6 Drawing Sheets

(51) Int. Cl.
*C07C 275/20* (2006.01)
*C08G 18/08* (2006.01)
*C08G 18/12* (2006.01)
*C08G 18/48* (2006.01)
*C08G 18/66* (2006.01)
*C09J 175/04* (2006.01)
*C08G 18/83* (2006.01)
*C09D 175/08* (2006.01)
*C09J 175/08* (2006.01)

(52) U.S. Cl.
CPC .............. *C08G 18/10* (2013.01); *C08G 18/12* (2013.01); *C08G 18/4812* (2013.01); *C08G 18/6692* (2013.01); *C08G 18/833* (2013.01); *C09D 175/08* (2013.01); *C09J 175/04* (2013.01); *C09J 175/08* (2013.01); *Y10T 156/10* (2015.01); *Y10T 428/31551* (2015.04)

(56) References Cited

U.S. PATENT DOCUMENTS

| | | | |
|---|---|---|---|
| 2005/0065276 A1* | 3/2005 | Burckhardt et al. | 524/589 |
| 2006/0052522 A1* | 3/2006 | Burckhardt et al. | 524/589 |
| 2007/0004893 A1 | 1/2007 | Burckhardt et al. | |
| 2007/0129522 A1 | 6/2007 | Burckhardt et al. | |

FOREIGN PATENT DOCUMENTS

| | | |
|---|---|---|
| JP | B-40-29011 | 12/1965 |
| WO | WO 95/24556 | 9/1995 |
| WO | WO 02/32562 A1 | 4/2002 |
| WO | WO 03/059978 A1 | 7/2003 |
| WO | WO 2004/013200 A1 | 2/2004 |
| WO | WO 2005/037885 A1 | 4/2005 |

\* cited by examiner

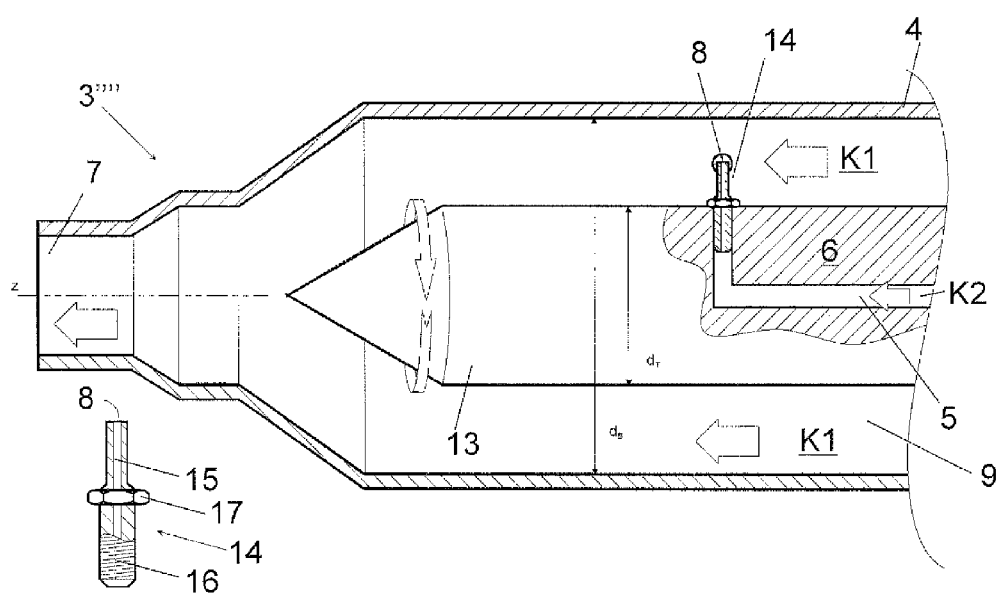
Figure 2 f')   Figure 2 f)

DIALDIMINE, EMULSION CONTAINING DIALDIMINE, AND BICOMPONENT POLYURETHANE COMPOSITION, AND THE USE THEREOF

This is a Division of application Ser. No. 12/449,739 filed Aug. 25, 2009, which in turn is a National Phase of Application No. PCT/EP2008/052729 filed Mar. 6, 2008. The disclosure of the prior applications is hereby incorporated by reference herein in its entirety.

FIELD OF THE INVENTION

The invention relates to the field of the polyaldimines, the aldimine-containing emulsions and the two-component polyurethane compositions.

PRIOR ART

Aldimines have long been used as blocked amines. In particular, polyaldimines are employed as latent curing agents in compositions which contain polymers having isocyanate groups and are used, for example, as adhesives or sealants. Such compositions cure on contact with water, aldehydes being liberated. These aldehydes generally have a very intense odour and are annoying and therefore greatly limit the potential uses of the compositions. WO 2004/013200 A1 discloses polyurethane compositions which contain polyaldimines and cure without an annoying odour.

One-component polyurethane compositions which contain polymers having isocyanate groups and cure with atmospheric humidity have long been used, for example as adhesives or sealants or as coatings. Since these compositions generally cure slowly, it has already often been proposed to accelerate the curing and hence also the increase in strength by admixing a second component which contains water. However, such two-component compositions have the major disadvantage that they tend to form bubbles. In the case of laminar mixing of the two components, they moreover often have reduced mechanical strength, particularly shortly after mixing. In the case of systems suitable in practice, the water-containing second component generally contains an organic VOC solvent, in particular an N-alkylpyrrolidone, which is associated with major disadvantages for occupational toxicology and occupational hygiene reasons.

WO 2005/037885 A1 describes two-component polyurethane compositions in which a second component which has low-odour polyaldimines in addition to water is mixed with a first component containing polyurethane prepolymers having isocyanate groups. It is true that these compositions show a reduction in bubbles and accelerated curing; however, their curing and their increase in strength are nevertheless still too slow for many applications.

SUMMARY OF THE INVENTION

The object of the present invention is therefore to provide a two-component polyurethane composition which overcomes the disadvantages of the prior art and in particular has high early strength.

Surprisingly, it has now been found that an emulsion which is based on dialdimines of the formula (I) is outstandingly suitable for use as a curing agent or accelerator component for polymers having isocyanate groups, in particular for polyurethanepolymers having isocyanate groups. In particular, it is possible to prepare therefrom pasty curing agent or accelerator compositions which lead to very high early strength, which have good flow behaviour on pumping and which can be formulated without VOC solvents, in particular without N-alkylpyrrolidones. These components can be mixed outstandingly homogeneously or inhomogeneously, in particular also in a laminar manner, with components which contain polyurethanepolymers having isocyanate groups, the two-component compositions thus obtained curing rapidly, having extremely high early strength and remaining without annoying weaknesses, in particular without weaknesses in or between the layers, especially when the layers are relatively thick. In spite of the rapid curing, these compositions, both in the case of laminar mixing and in the case of homogeneous mixing, have a sufficiently long open time which makes it possible reliably to carry out, for example, adhesive bonding.

The dialdimines of the formula (I) can be prepared in a targeted and simple manner from readily available dialdimines, diisocyanates and water.

Thus, the present invention relates to dialdimines of the formula, a process for the preparation thereof, emulsions containing such dialdimines, and the use thereof as curing agent component or accelerator component for an adhesive, sealant or coating material which contains polymers having isocyanate groups.

The invention furthermore relates to two-component compositions, the mixed or partly mixed compositions obtainable therefrom, the use of the two-component compositions as adhesive, sealant or coating or covering, processes for adhesive bonding, sealing or the production of a coating, and the articles resulting therefrom.

Preferred embodiments of the invention form the subject of the dependent claims.

DESCRIPTION OF THE PREFERRED EMBODIMENTS

The present invention relates to dialdimines of the formula (I).

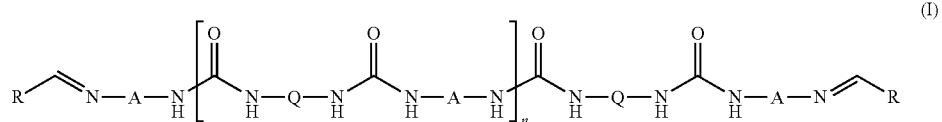

(I)

Here, R represents the radical of an aldehyde ALD after removal of an aldehyde group, and A represents the radical of a diamine DA having two primary aliphatic amino groups after removal of the two primary amino groups. The radicals A and R have no groups which are reactive with isocyanate groups in the absence of water, in particular no hydroxyl groups, no primary or secondary amino groups, no mercapto groups and no other groups having active hydrogen.

Furthermore, Q represents the radical of a diisocyanate DI after removal of both isocyanate groups, and n represents 0 or represents an integer from 1 to 15.

In the present document, the term "primary amino group" designates an $NH_2$ group which is bonded to an organic radical, while the term "secondary amino group" designates an NH group which is bonded to two organic radicals which may together be part of a ring.

An amino group which is bonded to an aliphatic, cycloaliphatic or arylaliphatic radical is designated as "aliphatic amino group". It therefore differs from an "aromatic amino group" which is bonded directly to an aromatic or heteroaromatic radical, such as, for example, in aniline or 2-aminopyridine.

In the present document, the term "polymer" comprises firstly a group of macromolecules which are chemically uniform but differ with respect to degree of polymerization, molar mass and chain length, which group of macromolecules was prepared by a polyreaction (polymerization, polyaddition, polycondensation). Secondly, the term also comprises derivatives of such a group of macromolecules from polyreactions, i.e. compounds which were obtained by reactions, such as, for example, additions or substitutions, of functional groups on predetermined macromolecules and which may be chemically uniform or chemically nonuniform. The term furthermore also comprises so-called prepolymers, i.e. reactive oligomeric preadducts, the functional groups of which are involved in the synthesis of macromolecules.

The term "polyurethanepolymer" comprises all polymers which are prepared by the so-called diisocyanate polyaddition process. This also includes those polymers which are virtually or completely free of urethane groups. Examples of polyurethanepolymers are polyether-polyurethanes, polyester-polyurethanes, polyether-polyureas, polyureas, polyester-polyureas, polyisocyanurates and polycarbodiimides.

A temperature of 25° C. is designated as "room temperature".

In the present document, substance names beginning with "poly", such as polyaldimine, polyisocyanate, polyol or polyaldehyde, designate substances which formally contain, per molecule, two or more of the functional groups occurring in their name.

In principle, all known aldehydes are suitable as aldehyde ALD. These aldehydes may be aliphatic, cycloaliphatic, arylaliphatic or aromatic aldehydes and may be monoaldehydes or polyaldehydes.

Suitable aliphatic, cycloaliphatic or arylaliphatic aldehydes ALD are, for example, propionaldehyde, butyraldehyde, isobutyraldehyde, 2-methyl-butyraldehyde, 2-ethylbutyraldehyde, valeraldehyde, isovaleraldehyde, 2-methylvaleraldehyde, 2,3-dimethylvaleraldehyde, hexanal, 2-ethylhexanal, octanal, isooctanal, nonanal, decanal, undecanal, 2-methylundecanal, dodecanal, cyclopropanecarboxaldehyde, cyclopentanecarboxaldehyd, cyclo-hexylcarboxaldehyde, 1,2,3,6-tetrahydrobenzaldehyde, phenylacetaldehyde, 2-phenylpropionaldehyde (hydratropaldehyde) and 2-methyl-3-phenylpropion-aldehyde.

Suitable aromatic aldehydes ALD are, for example, benzaldehyde, 2- and 3- and 4-tolualdehyde, 4-ethyl- and 4-propyl- and 4-isopropyl- and 4-butyl-benzaldehyde, 2,4-dimethylbenzaldehyde, 2,4,5-trimethylbenzaldehyde, 4-acetoxybenzaldehyde, 4-anisaldehyde, 4-ethoxybenzaldehyde, the isomeric di- and trialkoxybenzaldehydes, 2-, 3- and 4-nitrobenzaldehyde, 2- and 3- and 4-formylpyridine, 2-furfuraldehyde, 2-thiophenecarbaldehyde, 1- and 2-naphthylaldehyde, 3- and 4-phenyloxybenzaldehyde; quinoline-2-carbaldehyde and the 3-, 4-, 5-, 6-, 7- and 8-positional isomers thereof, anthracene-9-carbaldehyde, phthalaldehyde, isophthalaldehyde and terephthalaldehyde.

It has been found that in particular those aldehydes which contain no C—H group in the α-position relative to the carbonyl group and therefore cannot form tautomeric enols are suitable as aldehyde ALD.

The aldehyde ALD is therefore in particular an aldehyde of the formula (II-a) or an aldehyde of the formula (II-b).

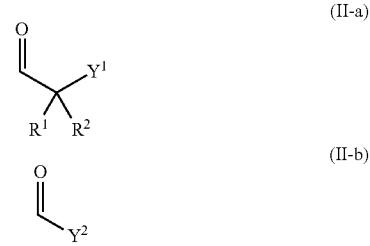

$R^1$ and $R^2$ either independently of one another each represent a monovalent hydrocarbon radical having 1 to 12 C atoms or together represent a divalent hydrocarbon radical having 4 to 20 C atoms, which is part of an optionally substituted carbocyclic ring having 5 to 8, preferably 6, C atoms;

$Y^1$ represents a monovalent hydrocarbon radical which optionally has at least one heteroatom, in particular oxygen in the form of ether, carbonyl or ester groups;

$Y^2$ represents either a substituted or unsubstituted aryl or heteroaryl group which has a ring size of 5 to 8, preferably 6, or represents

$R^6$ representing a hydrogen atom or representing an alkoxy group, or represents a substituted or unsubstituted alkenyl or arylalkenyl group having at least 6 C atoms.

Suitable aldehydes of the formula (II-a) are, for example, 2,2-dimethyl-propanal (pivalaldehyde), 2,2-dimethylbutanal, 2,2-diethylbutanal, 1-methyl-cyclopentanecarboxaldehyde, 1-methylcyclohexanecarboxaldehyde, and the ethers and esters of 2,2-disubstituted 3-hydroxypropanals, -butanals or analogous higher aldehydes, in particular of 2,2-dimethyl-3-hydroxypropanal, which ethers and esters are described further below.

Suitable aldehydes of the formula (II-b) are, for example, the aromatic aldehydes already mentioned as being suitable as aldehyde ALD, and glyoxal, glyoxylic acid esters, such as methyl glyoxylate, cinnamaldehyde and substituted cinnamaldehydes.

In a first embodiment, particularly suitable dialdimines of the formula (I) are those whose radicals R have the formula (II).

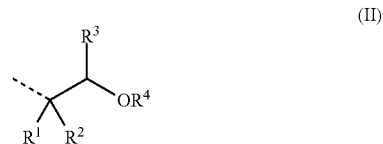

Here, $R^3$ represents a hydrogen atom or represents an alkyl or alkylaryl group, in particular having 1 to 12 C atoms; and $R^4$ represents a hydrocarbon radical optionally containing heteroatoms and having 1 to 30 C atoms.

In a second embodiment, particularly suitable dialdimines of the formula (I) are those whose radicals R have the formula (III).

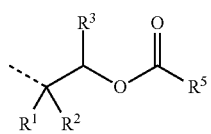

(III)

Here, $R^5$ represents either a linear or branched alkyl radical having 1 to 30 C atoms, optionally having cyclic moieties and optionally having at least one heteroatom, in particular oxygen, in the form of ether or carbonyl or esters groups, or represents a mono- or polyunsaturated linear or branched hydrocarbon radical having 1 to 30 C atoms.

These radicals R correspond to the formula (II), in which $R^4$ represents the radical of the formula (III').

(III')

Preferred dialdimines of the formula (I) are those which have a radical R of the formula (II) or formula (III) in which the radical $R^4$ represents a hydrocarbon radical optionally containing heteroatoms and having 11 to 30 C atoms; or in which the radical $R^5$ represents a linear or branched alkyl radical having 11 to 30 C atoms, optionally having cyclic moieties and optionally having at least one heteroatom, in particular oxygen in the form of ether or carbonyl or ester groups, or represents a mono- or polyunsaturated, linear or branched hydrocarbon radical having 11 to 30 C atoms.

These preferred dialdimines of the formula (I) are distinguished in that they themselves or the aldehydes formed on their hydrolysis are odourless. In this document, an "odourless" substance is understood as meaning a substance which has such little odour that it cannot be smelt by most human individuals, i.e. is not perceptible with the nose.

Particularly suitable aldehydes of the formula (II-a) are firstly aldehydes ALD1 of the formula (II-a'), i.e. aldehydes ALD having the radical R of the formula (II).

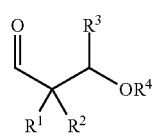

(II-a')

The aldehydes ALD1 of the formula (II-a') are ethers of aliphatic, arylaliphatic or cycloaliphatic 2,2-disubstituted 3-hydroxyaldehydes with alcohols or phenols of the formula $R^4$—OH, for example fatty alcohols or phenols. Suitable 2,2-disubstituted 3-hydroxyaldehydes are in turn obtainable from aldol reactions, in particular crossed aldol reactions, between primary or secondary aliphatic aldehydes, in particular formaldehyde, and secondary aliphatic, secondary arylaliphatic or secondary cycloaliphatic aldehydes, such as, for example 2-methylbutyraldehyde, 2-ethylbutyraldehyde, 2-methyl-valeraldehyde, 2-ethylcapronaldehyde, cyclopentanecarboxaldehyde, cyclohexanecarboxaldehyde, 1,2,3,6-tetrahydrobenzaldehyde, 2-methyl-3-phenylpropionaldehyde, 2-phenylpropionaldehyde (hydratropaldehyde) or diphenylacetaldehyde. Examples of suitable 2,2-disubstituted 3-hydroxy-aldehydes are 2,2-dimethyl-3-hydroxypropanal, 2-hydroxymethyl-2-methyl-butanal, 2-hydroxymethyl-2-ethylbutanal, 2-hydroxymethyl-2-methylpentanal, 2-hydroxymethyl-2-ethylhexanal, 1-hydroxymethylcyclopentanecarbox-aldehyde, 1-hydroxymethylcyclohexanecarboxaldehyde, 1-hydroxy-methylcyclohex-3-enecarboxaldehyde, 2-hydroxymethyl-2-methyl-3-phenyl-propanal, 3-hydroxy-2-methyl-2-phenylpropanal and 3-hydroxy-2,2-diphenyl-propanal.

Examples of aldehydes ALD1 of the formula (II-a') are 2,2-dimethyl-3-phenoxypropanal, 3-cyclohexyloxy-2,2-dimethylpropanal, 2,2-dimethyl-3-(2-ethylhexyloxy)propanal, 2,2-dimethyl-3-lauryloxypropanal and 2,2-dimethyl-3-stearyloxypropanal.

Particularly suitable aldehydes of the formula (II-a) are secondly aldehydes ALD2 of the formula (II-a''), i.e. aldehydes ALD having the radical R of the formula (III).

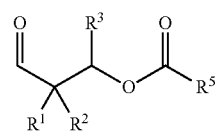

(II-a'')

The aldehydes ALD2 of the formula (II-a'') are esters of the already described 2,2-disubstituted 3-hydroxyaldehydes with suitable carboxylic acids.

Examples of suitable carboxylic acids are saturated aliphatic carboxylic acids, such as formic acid, acetic acid, propionic acid, butyric acid, isobutyric acid, valeric acid, caproic acid, 2-ethylcaproic acid, oenanthic acid, caprylic acid, pelargonic acid, capric acid, undecanoic acid, lauric acid, tridecanoic acid, myristic acid, pentadecanoic acid, palmitic acid, margaric acid, stearic acid, nonadecanoic acid, arachidic acid; monounsaturated aliphatic carboxylic acids, such as palmitoleic acid, oleic acid, erucic acid; polyunsaturated aliphatic carboxylic acids, such as linoleic acid, linolenic acid, elaeostearic acid, arachidonic acid; cycloaliphatic carboxylic acids, such as cyclohexanecarboxylic acid; arylaliphatic carboxylic acids, such as phenylacetic acid, aromatic carboxylic acids, such as benzoic acid, naphthoic acid, toluic acid, anisic acid; isomers of these acids; fatty acid mixtures from the industrial saponification of natural oils and fats, such as, for example, rapeseed oil, sunflower oil, linseed oil, olive oil, coconut oil, palm kernel oil and palm oil; and dicarboxylic acid monoalkyl and monoaryl esters, as are obtained from the monoesterification of dicarboxylic acids, such as succinic acid, glutaric acid, adipic acid, pimelic acid, suberic acid, azelaic acid, sebacic acid, 1,12-dodecanedioic acid, maleic acid, fumaric acid, hexahydrophthalic acid, hexahydroisophthalic acid, hexahydroterephthalic acid, 3,6,9-trioxaundecane-dioic acid and similar derivatives of polyethylene glycol, with alcohols, such as methanol, ethanol, propanol, butanol, higher homologues and isomers of these alcohols.

Preferred aldehydes ALD2 of the formula (II-a") are 3-benzoyloxy-2,2-dimethylpropanal, 3-cyclohexanoyloxy-2,2-dimethylpropanal, 2,2-dimethyl-3-(2-ethylhexyloxy) propanal, 2,2-dimethyl-3-lauroyloxypropanal, 2,2-dimethyl-3-myristoyloxypropanal, 2,2-dimethyl-3-palmitoyloxypropanal, 2,2-dimethyl-3-stearoyloxypropanal and analogous esters of other 2,2-disubstituted 3-hydroxy-aldehydes.

In a particularly preferred embodiment, $R^5$ is selected from the group consisting of phenyl, cyclohexyl, 2-ethylhexyl and the $C_{11}$-, $C_{13}$-, $C_{15}$- and $C_{17}$-alkyl groups.

In general, 2,2-dimethyl-3-lauroyloxypropanal is preferred as aldehyde ALD2 of the formula (II-a").

In a preferred method for the preparation of the aldehyde ALD2 of the formula (II-a"), a 2,2-disubstituted 3-hydroxyaldehyde, in particular 2,2-di-methyl-3-hydroxypropanal, which can be prepared, for example, from formaldehyde (or paraformaldehyde) and isobutyraldehyde, optionally in situ, is reacted with a carboxylic acid to give the corresponding ester. This esterification can be effected without the use of solvents by known methods, described, for example, in Houben-Weyl, "Methoden der organischen Chemie [Methods of Organic Chemistry]", Vol. VIII, pages 516-528.

The aldehydes ALD2 of the formula (II-a") are preferred to the aldehydes ALD1 of the formula (II-a'), owing to their simple preparability.

In a particularly preferred embodiment, the aldehyde ALD is odourless. Odourless aldehydes ALD are firstly in particular aldehydes ALD1 of the formula (II-a'), in which the radical $R^4$ represents a hydrocarbon radical having 11 to 30 C atoms, which optionally contains heteroatoms.

Secondly, odourless aldehydes ALD are in particular aldehydes ALD2 of the formula (II-a') in which the radical $R^5$ either represents a linear or branched alkyl group having 11 to 30 carbon atoms, optionally with cyclic moieties, and optionally with at least one heteroatom, in particular with at least one ether oxygen, or represents a mono- or polyunsaturated linear or branched hydrocarbon chain having 11 to 30 carbon atoms.

Examples of odourless aldehydes ALD2 of the formula (II-a") are esterification products of the abovementioned 2,2-disubstituted 3-hydroxy-aldehydes with carboxylic acids, such as, for example, lauric acid, tridecanoic acid, myristic acid, pentadecanoic acid, palmitic acid, margaric acid, stearic acid, nonadecanoic acid, arachidic acid, palmitoleic acid, oleic acid, erucic acid, linoleic acid, linolenic acid, elaeostearic acid, arachidonic acid, and fatty acid mixtures from the industrial saponification of natural oils and fats, such as, for example, rapeseed oil, sunflower oil, linseed oil, olive oil, coconut oil, palm kernel oil and palm oil.

Preferred odourless aldehydes ALD2 are 2,2-dimethyl-3-lauroyloxypropanal, 2,2-dimethyl-3-myristoyloxypropanal, 2,2-dimethyl-3-palmitoyloxypropanal and 2,2-dimethyl-3-stearoyloxypropanal. 2,2-Dimethyl-3-lauroyloxypropanal is particularly preferred.

The diamine DA having two primary aliphatic amino groups has two primary amino groups which are bonded to an aliphatic, cycloaliphatic or arylaliphatic radical.

Aliphatic, cycloaliphatic or arylaliphatic diamines are suitable as diamine DA, for example ethylenediamine, 1,2-propanediamin, 1,3-propanediamine, 2-methyl-1,2-propanediamine, 2,2-dimethyl-1,3-propanediamine, 1,3-butanediamine, 1,4-butanediamine, 1,3-pentanediamine (DAMP), 1,5-pentanediamine, 1,5-diamino-2-methylpentane (MPMD), 1,6-hexanediamine, 2,5-dimethyl-1,6-hexanediamine, 2,2,4-trimethylhexa-methylenediamine, 2,4,4-trimethylhexamethylenediamine, 1,7-heptanediamine, 1,8-octanediamine, 1,9-nonanediamine, 1,10-decanediamine, 1,11-undecane-diamine, 1,12-dodecanediamine and methylbis(3-aminopropyl)amine, 1,2-, 1,3- and 1,4-diaminocyclohexane, bis(4-aminocyclohexyl)methane, bis(4-amino-3-methylcyclohexyl)methane, bis(4-amino-3-ethylcyclohexyl)methane, bis(4-amino-3,5-dimethylcyclohexyl)methane, 1-amino-3-aminomethyl-3,5,5-tri-methylcyclohexane (=isophoronediamine or IPDA), 2- and 4-methyl-1,3-diaminocyclohexane and mixtures thereof, 1,3- and 1,4-bis(aminomethyl)-cyclohexane, 1-cyclohexylamino-3-aminopropane, 2,5(2,6)-bis(aminomethyl)-bicyclo[2.2.1]heptane (NBDA, produced by Mitsui Chemicals), 3(4),8(9)-bis (aminomethyl)tricyclo[5.2.1.0$^{2,6}$] decane, 1,4-diamino-2,2,6-trimethylcyclo-hexane (TMCDA), 3,9-bis(3-aminopropyl)-2,4,8,10-tetraoxaspiro[5.5] undecane and 1,3- and 1,4-xylylenediamine.

Aliphatic diamines containing ether groups are particularly suitable as diamine DA, for example bis(2-aminoethyl) ether, 3,6-dioxaoctane-1,8-diamine, 4,7-dioxadecane-1,10-diamine, 4,7-dioxadecane-2,9-diamine, 4,9-dioxadodecane-1,12-diamine, 5,8-dioxadodecane-3,10-diamine and higher oligomers of these diamines, and polyoxyalkylenediamines. The latter are typically products from the amination of polyoxyalkylenediols and are obtainable, for example, under the name Jeffamine® (from Huntsman Chemicals), under the name polyetheramine (from BASF) or under the name PC Amine® (from Nitroil). Particularly suitable polyoxyalkylenediamines are Jeffamine® D-230, Jeffamine® D-400, Jeffamine® D-2000, Jeffamine® D-4000, Jeffamine® XTJ-511, Jeffamine® ED-600, Jeffamine® ED-900, Jeffamine® ED-2003, Jeffamine® XTJ-568, Jeffamine® XTJ-569, Jeffamine® XTJ-523, Jeffamine® XTJ-536, Jeffamine® XTJ-542, Jeffamine® XTJ-559; polyetheramine D 230, polyetheramine D 400 and polyetheramine D 2000, PC Amine® DA 250, PC Amine® DA 400, PC Amine® DA 650 and PC Amine® DA 2000.

Aliphatic diamines containing ether groups are preferred as diamine DA, in particular an aliphatic diamine which contains ether groups and is selected from the group consisting of bis(2-aminoethyl)ether, 3,6-dioxaoctane-1,8-diamine, 4,7-dioxadecane-1,10-diamine, 4,7-dioxadecane-2,9-diamine, 4,9-dioxadodecane-1,12-diamine, 5,8-dioxadodecane-3,10-diamine and higher oligomers of these diamines, and polyoxyalkylenediamines of the formula (V').

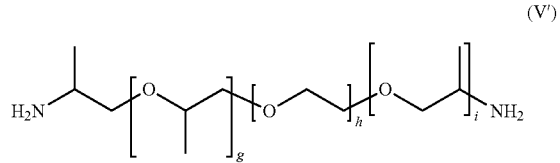

(V')

Here, g, h and i each represent 0 or an integer from 1 to 40, with the proviso that the sum of g, h and i is ≥1.

The diamine DA of the formula (V') preferably has a molecular weight between 200 and 5000 g/mol.

Examples of polyoxyalkylenediamines of the formula (V') are the commercially available types Jeffamine® D-230, Jeffamine® D-400, Jeffamine® D-2000, Jeffamine® D-4000, Jeffamine® XTJ-511, Jeffamine® ED-600, Jeffamine® ED-900 and Jeffamine® ED-2003 (all from Huntsman Chemical); polyetheramine D 230, polyetheramine D 400 and polyetheramine D 2000 (all from BASF); and PC Amine® DA 250, PC Amine® DA 400, PC Amine® DA 650 and PC Amine® DA 2000 (all from Nitroil).

The diisocyanate DI is either a monomeric diisocyanate or an oligomeric derivative thereof, or a polyurethanepolymer P having isocyanate groups.

Suitable monomeric diisocyanates or oligomeric derivatives thereof are, for example, 1,6-hexamethylene diisocyanate (HDI), 2-methylpenta-methylene-1,5-diisocyanate, 2,2, 4- and 2,4,4-trimethyl-1,6-hexamethylene diisocyanate (TMDI), 1,10-decamethylene diisocyanate, 1,12-dodecamethylene diisocyanate, lysine and lysine ester diisocyanate, cyclohexane 1,3-diisocyanate, cyclohexane 1,4-diisocyanate and any mixturers of these isomers, 1-methyl-2,4- and -2,6-diisocyanatocyclohexane and any mixtures of these isomers (HTDI or $H_6TDI$), 1-isocyanato-3,3,5-trimethyl-5-isocyanato-methylcyclohexane (=Isophorone diisocyanate or IPDI), perhydro-2,4'-diphenylmethane diisocyanate and perhydro-4,4'-diphenylmethane diisocyanate (HMDI or $H_{12}MDI$), 1,4-diisocyanato-2,2,6-trimethylcyclohexane (TMCDI), 1,3- and 1,4-bis(isocyanatomethyl)cyclohexane, m- and p-xylylene diisocyanate (m- and p-XDI), m- and p-tetramethyl-1,3- and -1,4-xylylene diisocyanate (m- and p-TMXDI), bis(1-isocyanato-1-methylethyl)naphthalene, 2,4- and 2,6-toluene diisocyanate and any mixtures of these isomers (TDI), 4,4'-, 2,4'- and 2,2'-diphenylmethane diisocyanate and any mixtures of these isomers (MDI), 1,3- and 1,4-phenylene diisocyanate, 2,3,5,6-tetramethyl-1,4-diisocyanatobenzene, naphthalene 1,5-diisocyanate (NDI), 3,3'-dimethyl-4,4'-diisocyanatobiphenyl (TOBI), dianisidine diisocyanate (DADI), oligomers of the abovementioned isocyanates, for example in the form of uretdiones, allophanates and oxadiazinetriones or in the form of adducts with short-chain polyols, and any mixtures of the abovementioned isocyanates and oligomers.

MDI, TDI, HDI and IPDI are preferred. MDI and TDI are particularly preferred.

The diisocyanate DI is preferably a polyurethanepolymer P having isocyanate groups.

Suitable polyurethanepolymers P having isocyanate groups have two isocyanate groups and are a product from the reaction of at least one diol with at least one diisocyanate, in particular with at least one diisocyanate which is selected from the monomeric diisocyanates described above. In particular, an aromatic diisocyanate, in particular 2,4- or 2,6-toluene diisocyanate (TDI) or 4,4'-, 2,4'- or 2,2'-diphenylmethane diisocyanate (MDI), is preferred as the monomeric diisocyanate.

Diols suitable for the reaction to give the polyurethanepolymer P having isocyanate groups are in particular polyetherdiols, polyesterdiols and polycarbonatediols, and mixtures of these diols.

Suitable polyetherdiols, also referred to as polyoxyalkylenediols, are in particular those which are polymerization products of ethylene oxide, 1,2-propylene oxide, 1,2- or 2,3-butylene oxide, tetrahydrofuran or mixtures thereof, possibly polymerized with the aid of a starter molecule having two active hydrogen atoms, such as, for example, water, 1,2-ethanediol, 1,2- and 1,3-propanediol, neopentylglycol, diethylene glycol, triethylene glycol, the isomeric dipropylene glycols and tripropylene glycols, the isomeric butanediols, pentanediols, hexanediols, heptanediols, octanediols, nonanediols, decanediols, undecanediols, 1,3- and 1,4-cyclohexanedimethanol, bisphenol A, hydrogenated bisphenol A, aniline, and short-chain polyetherdiols, and mixtures of the abovementioned compounds. Both polyoxyalkylenediols which have a low degree of unsaturation (measured according to ASTM D-2849-69 and stated in milliequivalents of unsaturation per gram of diol (meq/g)), prepared, for example, with the aid of so-called double metal cyanide complex catalysts (DMC catalysts), and polyoxyalkylenediols having a higher degree of unsaturation, prepared, for example, with the aid of anionic catalysts, such as NaOH, KOH or alkali metal alcoholates, may be used.

Particularly suitable polyoxyalkylenediols are polyoxyethylenediols and polyoxypropylenediols.

Polyoxypropylenediols having a degree of unsaturation lower than 0.02 meq/g and a molecular weight in the range of 1000 to 30 000 g/mol and polyoxypropylenediols having a molecular weight of 400 to 8000 g/mol are particularly suitable. In the present document, "molecular weight" is always understood as meaning the weight average molecular weight $M_n$. Polyoxypropylenediols having a degree of unsaturation lower than 0.02 meq/g and a molecular weight in the range of 1000 to 12 000 g/mol, in particular between 1000 and 8000 g/mol, are particularly suitable. Such polyetherdiols are sold, for example, under the trade name Acclaim® by Bayer.

Also particularly suitable are so-called "EO-endcapped" (ethylene oxide-endcapped) polyoxypropylenediols. The latter are special polyoxy-propylenepolyoxyethylenediols which are obtained, for example, by a procedure in which pure polyoxypropylenediols are alkoxylated with ethylene oxide after completion of the polypropoxylation and thereby have primary hydroxyl groups.

Suitable polyesterdiols are polyesters which carry two hydroxyl groups and are prepared by known processes, in particular the polycondensation of hydroxycarboxylic acids or the polycondensation of aliphatic and/or aromatic dicarboxylic acids with dihydric alcohols.

Particularly suitable are polyesterdiols which are prepared from dihydric alcohols, such as, for example, ethylene glycol, diethylene glycol, propylene glycol, dipropylene glycol, neopentylglycol, 1,4-butanediol, 1,5-pentanediol, 3-methyl-1,5-hexanediol, 1,6-hexanediol, 1,8-actanediol, 1,10-decanediol, 1,12-dodecanediol, 1,12-hydroxystearyl alcohol, 1,4-cyclohexanedimethanol, dimer fatty acid diol (dimer diol), neopentylglycol hydroxypivalate or mixtures of the abovementioned alcohols, with organic dicarboxylic acids or anhydrides or esters thereof, such as, for example, succinic acid, glutaric acid, adipic acid, trimethyladipic acid, suberic acid, azelaic acid, sebacic acid, dodecanedicarboxylic acid, maleic acid, fumaric acid, dimer fatty acid, phthalic acid, phthalic anhydride, isophthalic acid, terephthalic acid, dimethyl terephthalate, hexahydrophthalic acid or mixtures of the abovementioned acids, and polyesterdiols obtained from lactons, such as, for example, from ε-caprolactone, and starters, such as the abovementioned dihydric alcohols.

Particularly suitable polyesterdiols are those which are prepared from adipic acid, azelaic acid, sebacic acid, dodecanedicarboxylic acid, dimer fatty acid, phthalic acid, isophthalic acid and terephthalic acid as the dicarboxylic acid and from ethylene glycol, diethylene glycol, neopentylglycol, 1,4-butanediol, 1,6-hexanediol, dimer fatty acid diol and 1,4-cyclohexane-dimethanol as the dihydric alcohol. Also particularly suitable are polyesterdiols prepared from ε-caprolactone and one of the abovementioned dihydric alcohols as the starter.

The polyesterdiols advantageously have a molecular weight of 1000 to 15 000 g/mol, in particular of 1500 to 8000 g/mol, especially of 1700 to 5500 g/mol.

Amorphous, semicrystalline and crystalline polyesterdiols which are liquid at room temperature are particularly suitable. Polyesterdiols which are liquid at room temperature and mixtures of amorphous polyesterdiols which are liquid at room temperature are particularly suitable.

Suitable polycarbonatediols are those which are obtainable by polycondensation, for example of the abovementioned dihydric alcohols—used for the synthesis of the polyesterdiols—with dialkyl carbonates, such as dimethyl carbonate, diaryl carbonates, such as diphenyl carbonate, or phosgene.

Polycarbonatediols which are liquid or amorphous at room temperature are particularly suitable.

Diols furthermore suitable for the reaction to give the polyurethanepolymer P having isocyanate groups are block copolymers which carry two hydroxyl groups and have at least two different blocks having a polyether, polyester and/or polycarbonate structure of the type described above.

Diols preferred for the reaction to give the polyurethanepolymer P having isocyanate groups are polyoxyalkylenediols, in particular polyoxyethylenediols, polyoxypropylenediols and polyoxypropylene-polyoxyethylenediols.

The preparation of the polyurethanepolymer P having isocyanate groups is effected in a manner known per se, either directly from the diisocyanates and the diols or by stepwise addition processes, also known as chain extension reactions.

In a preferred embodiment, the polyurethanepolymer P having isocyanate groups is prepared by the reaction of at least one diisocyanate with at least one diol, the isocyanate groups being present in stoichiometric excess relative to the hydroxyl groups. Advantageously, the ratio between isocyanate groups and hydroxyl groups is from 1.3 to 2.5, in particular from 1.5 to 2.2.

The dialdimine of the formula (I) preferably has a molecular weight of 1000 to 30 000 g/mol, in particular of 2000 to 30 000 g/mol, preferably of 4000 to 30 000 g/mol, most preferably of 6000 to 20 000 g/mol.

The dialdimine of the formula (I) can be prepared by the process described below, which is a further aspect of the invention.

This process comprises the step of reacting a diisocyanate DI with a dialdimine of the formula (IV), in particular of the formula (IV') or of the formula (IV"), in the presence of water.

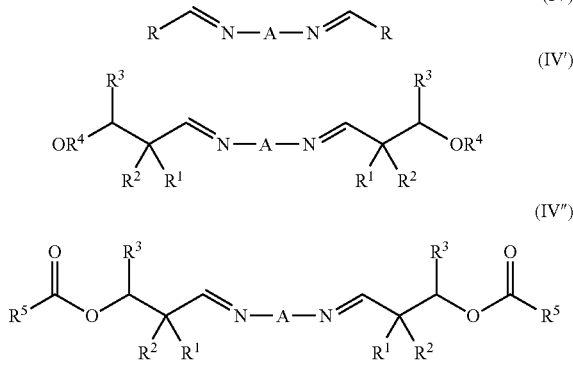

The radicals R, A, $R^1$, $R^2$, $R^3$ and $R^4$ and $R^5$ have already been described.

This reaction is carried out in such a way that the molar ratio $$\frac{[\text{diisocyanate } DI]}{[\text{dialdimine of the formula }(IV) \text{ or }(IV') \text{ or }(IV'')]}$$

has a value of <1,
in particular of 0.9 to 0.5, preferably of 0.8 to 0.5. Furthermore, the amount of water is chosen so that the molar ratio of [water]/[diisocyanate DI] is ≥2, preferably ≥10.

The chosen value of the molar ratio of [diisocyanate DI]/[dialdimine of the formula (IV) or (IV') or (IV")] directly determines the average chain length, i.e. the magnitude of n in formula (I) and hence the average molecular weight of the dialdimine of the formula (I). The closer the value of the ratio is to 1, the greater is the extent of the chain extension reaction and the higher therefore is the average molecular weight of the dialdimine of the formula (I).

In the preparation of the dialdimine of the formula (I), preferably the diisocyanate DI is first mixed with the dialdimine of the formula (IV) or (IV') or (IV") and water is then added.

In this reaction, at least one aldehyde ALD of the formula R—CHO is liberated.

The dialdimine of the formula (I) is used in particular in the form of an emulsion.

A further aspect of the present invention therefore relates to an aldimine-containing emulsion.

The aldimine-containing emulsion comprises
a) at least one dialdimine of the formula (I) as described above;
b) water; and
c) optionally at least on surfactant.

It is also possible for the aldimine-containing emulsion to consist of a), b) and optionally c).

An aldimine-containing emulsion preferably comprises at least one surfactant.

Surfactants which may be used are natural or synthetic substances which reduce the surface tension of the water or other liquids in solutions. Anionic, cationic, nonionic or ampholytic surfactants or mixtures thereof may be used as surfactants, also referred to as wetting agents.

Examples of anionic surfactants are compounds having carboxylate, sulphate, phosphate or sulphonate groups, such as, for example, fatty alcohol ethers sulphates, fatty alcohol sulphates, soaps, alkanesulphonates, olefin-sulphonates, arylsulphonates, alkylarylsulphonates and alkyl phosphates.

Examples of cationic surfactants are quaternary ammonium or phosphonium compounds, such as, for example, tetraalkylammonium salts, dimethyldistearylammonium salts and N-alkylpyridinium salts, in particular the chlorides thereof.

The nonionic surfactants, the so-called niotensides, include, for example, ethoxylates of alcohols, phenols, alkylphenols, amines, fatty amines, fatty acids, fatty acid amides, polysiloxanes and fatty acid esters, also alkyl or alkylphenyl polyglycol ethers, such as, for example, fatty alcohol polyglycol ethers, or fatty acid amides, alkyl glycosides, sugar esters, sorbitan esters, polysorbates or trialkylamine oxides, also esters and amides of poly(meth)acrylic acids with polyalkylene glycols or aminopolyalkylene glycols, which may be blocked at one end with alkyl groups.

The ampholytic or amphoteric surfactants include amphoteric electrolytes, so-called ampholytes, such as, for example, aminocarboxylic acids, and betaines.

Such surfactants are widely available commercially.

Anionic surfactants have proved to be particularly suitable.

Advantageously, the aldimine-containing emulsion is obtained by adding water and optionally the surfactant to the dialdimine of the formula (I) with stirring.

It is clear to the person skilled in the art that the aldimine-containing emulsion can also be prepared otherwise.

It is true that it is known to the person skilled in the art that, in the preparation of an emulsion, various parameters, such as temperature, stirring speed and type and geometry of the stirring instruments, have an important influence on the quality of the emulsion. However, it was found that these parameters tend not to be critical in the preparation of the aldimine-containing emulsion discussed here. Thus, the aldimine-containing emulsion could be prepared rapidly, reproducibly and in good quality on a very wide range of stirring units without major adaptation of the stirring parameters.

It may furthermore be advantageous if the aldimine-containing emulsion comprises further constituents. Coemulsifiers, antifoams, stabilizers, biocides, such as fungicides, bactericides or algicides, adhesion promoters, solvents, plasticizers, catalysts, fillers and rheology auxiliaries, in particular thickeners and thixotropic agents, may be mentioned in particular as further constituents.

The aldimine-containing emulsion may or may not have organic solvents. If organic solvents are used, it is advantageous if they are not VOC solvents (VOC=volatile organic compounds). However, there are many different definitions of "volatile organic compounds" or "VOC". Thus, for example, according to EU Directive 2004/42/EC, a VOC is defined as an organic compound having a boiling point of not more than 250° C. at a standard pressure of 101.3 kPa. According to the Swiss ordinance relating to the steering tax on volatile organic compounds, VOC are defined as organic compounds having a vapour pressure of at least 0.1 mbar at 20° C. or a boiling point of not more than 240° C. at 1013.25 mbar. In the present document, organic compounds which have a boiling point of not more than 250° C. at atmospheric pressure (1013 mbar) or a vapour pressure of at least 0.1 mbar at 20° C. are considered to be "volatile organic compounds" or "VOC".

In particular, those solvents which are not VOC are carboxylic acid esters.

The aldimine-containing emulsion is preferably free of N-alkyl-pyrrolidones. In particular, the aldimine-containing emulsion contains no N-methylpyrrolidone (NMP).

Suitable catalysts are in particular tertiary amines, in, particular trialkylamines, such as, for example, triethylamine, and morpholine ether derivatives, such as dimorpholinodiethyl ether, tetramethyldimorpholinodiethyl ether, polyethylene glycol dimorphonlino ether and the like.

It has proved to be particularly advantageous if the aldimine-containing emulsion additionally has at least one surfactant, at least one filler, in particular a chalk or a pyrogenic silica, apart from at least one dialdimine of the formula (I) and water. Furthermore, the aldimine-containing emulsion preferably has at least one catalyst.

Preferably, the aldimine-containing emulsion has a pasty consistency, i.e. it is not self-flowing.

The aldimine-containing emulsion is stable and can be packed and stored. During the storage of the aldimine-containing emulsion, however, it should be ensured that the temperature does not fall below the freezing point of the emulsion since otherwise there is the danger that the emulsion will break. A broken emulsion can have serious disadvantages when it is used.

The aldimine-containing emulsion described has a wide range of uses. In a preferred embodiment, the aldimine-containing emulsion is used as a curing agent component or as an accelerator component for an adhesive, sealant or coating material which contains polymers having isocyanate groups, in particular polyurethanepolymers having isocyanate groups.

In a further aspect, the present invention therefore relates to a two-component composition which consists of the two components C1 and C2.

The first component, component C1, contains at least one polymer having isocyanate groups, in particular at least one polyurethanepolymer P having isocyanate groups, as described above, or consists thereof.

The second component, component C2, contains a dialdimine of the formula (I), as described above, or an aldimine-containing emulsion, as described above, or consists thereof.

Advantageously, the component C1 contains at least one filler. The filler influences, for example, both the consistency of the uncured composition and the mechanical properties of the cured composition. Suitable fillers are inorganic and organic fillers, for example natural, ground or precipitated calcium carbonates, which are optionally coated with fatty acids, in particular stearates, calcined kaolins, aluminas, aluminium hydroxides, barite ($BaSO_4$, also referred to as heavy spar), silicas, in particular colloidal silicas from pyrolysis processes, carbon blacks, in particular industrially produced carbon blacks (referred to as "carbon black" below), PVC powders or hollow spheres. Preferred fillers are calcium carbonates, kaolins, pyrogenic silicas and carbon black. It may be advantageous to use a mixture of different fillers.

A suitable amount of filler is, for example, in the range of 10 to 70% by weight, preferably 20 to 60% by weight, based on the total component C1.

Advantageously, the component C1 furthermore contains at least catalyst which accelerates the reaction of the isocyanate groups and/or the hydrolysis of the aldimine groups.

Catalysts which accelerate the reaction of the isocyanate groups with water are in particular metal compounds, for example tin compounds, such as dibutyltin diacetate, dibutyltin dilaurate, dibutyltin distearate, dibutyltin diacetylacetonate, dioctyltin dilaurate, dibutyltin dichloride and dibutyltin oxide, tin(II) carboxylates, stannoxanes, such as laurylstannoxane, bismuth compounds, such as bismuth(III) octanoate, bismuth(III) neodecanoate or bismuth(III) oxinates; and tertiary amines, for example 2,2'-dimorpholinodiethyl ether and other morpholine ether derivatives.

Catalysts which accelerate the hydrolysis of aldimine groups are in particular acids or compounds which can be hydrolyzed to give acids, for example organic carboxylic acids, such as benzoic acid, salicylic acid or 2-nitrobenzoic acid, organic carboxylic anhydrides, such as phthalic anhydride or hexahydrophthalic anhydride, silyl esters of organic carboxylic acids, organic sulphonic acids, such as methanesulphonic acid, p-toluenesulphonic acid or 4-dodecylbenzenesulphonic acid, or further organic or inorganic acids.

Combinations of said catalysts may also be present, in particular mixtures of acids and metal compounds, or of metal compounds and tertiary amines, or of acids and tertiary amines, or of acids and metal compounds and tertiary amines.

A typical catalyst content is 0.005 to 1% by weight, based on the total component C1, amounts used and catalysts which are expedient for this purpose being clear to the person skilled in the art.

Advantageously, the component C1 furthermore contains at least one plasticizer. Suitable plasticizers are, for example, esters of organic carboxylic acids or anhydrides thereof, phthalates, such as dioctyl phthalate, diisononyl phthalate or diisodecyl phthalate, adipates, such as dioctyl adipate, azelates and sebacates; organic phosphoric and sulphonic acid esters and polybutenes.

Further possible constituents of the component C1 are, inter alia, the following auxiliaries and additives:
- solvents, in particular solvents which are not VOC;
- fibres, for example comprising polyethylene;
- pigments, for example titanium dioxide or iron oxides;
- further catalysts customary in polyurethane chemistry;
- rheology modifiers, such as, for example, thickeners or thixotropic agents, for example urea compounds, polyamide waxes, bentonites or pyrogenic silicas;
- reactive diluents or crosslinking agents, for example oligomers or polymers of diisocyanates, such as MDI, PMDI, TDI, HDI, 1,12-dodecamethylene diisocyanate, cyclohexane 1,3- or 1,4-diisocyanate, IPDI, perhydro-2,4'- and -4,4'-diphenylmethane diisocyanate ($H_{12}MDI$), 1,3- and 1,4-tetramethyl-xylylene diisocyanate, in particular isocyanurates, carbodiimides, uretonimines, biurets, allophanates and iminooxadiazinediones of said diisocyanates, adducts of diisocyanates with short-chain polyols, adipic acid dihydrazide and other dihydrazides, and blocked curing agents in the form of polyaldimines, polyketimines, oxazolidines or polyoxazolidines;
- drying agents, such as, for example, molecular sieves, calcium oxide, highly reactive isocyanates, such as p-tosyl isocyanate, othoformic acid esters, alkoxysilanes, such as tetraethoxysilane, organoalkoxysilanes, such as vinyltrimethoxysilane, and organoalkoxysilanes which have a functional group in the α-position to the silane group;
- adhesion promoters, in particular organoalkoxysilanes, referred to below as "silanes", such as, for example, epoxysilanes, vinylsilanes, (meth)acryloylsilanes, isocyanatosilanes, carbamatosilanes, S-(alkyl-carbonyl) mercaptosilanes and aldiminosilanes, and oligomeric forms of these silanes;
- heat, light and UV stabilizers;
- flame-retardant substances;
- surface-active substances, such as, for example, wetting agents, levelling agents, deaerating agents or antifoams;
- biocides, such as, for example, algicides, fungicides or substances which inhibit fungal growth;

and further substances customarily used in one-component polyurethane compositions.

Advantages of the present invention are particularly clearly evident in cases where the component C1 contains both fillers and polyaldimines as further constituents.

It is advantageous to choose all of said substituents optionally present in the component C1, in particular a filler, a catalyst and a plasticizer, so that the shelf-life of the component C1 is not impaired by the presence of such a constituent, i.e. the component C1 does not change or changes only slightly in its properties, in particular the application and curing properties, during storage. This requires that reactions leading to chemical curing of the component C1, in particular of the isocyanate groups, do not occur to a significant extent during the storage. It is therefore particularly important that said constituents contain not water or at most traces of water or liberate no water or at most traces of water during storage. It may be expedient to dry certain constituents chemically or physically before mixing into the component C1.

The component C1 is prepared and stored in the absence of moisture. In a suitable, airtight packaging or arrangement, such as, for example, in a drum, a bag or a cartridge, it has an outstanding shelf-life. The term "having a shelf-life" and "shelf-life" in association with a composition designate in the present document the fact that the viscosity of the composition at a given application temperature and on suitable storage does not increase in the time span considered or at most increases in the time span considered to such an extent that the composition remains usable in the intended manner.

Typically, the component C1 is a moisture-curing one-component polyurethane adhesive or sealant, such as are widely available commercially. For example, such adhesives are available under the name Sikaflex® or SikaTack® from Sika Schweiz AG.

On its own, i.e. without component C2, the component C1 reacts with atmospheric moisture and cures thereby. However, this curing is very slow; moreover, bubble formation occasionally occurs during such curing. However, the curing is greatly accelerated and the bubble formation suppressed by the described use of the second (aldimine-containing) component C2.

The component C2 may contain further constituents, in particular those as mentioned above for the component C1, provided that these further constituents have a long shelf-life with the other constituents of the component C2. After the preparation, the component C2 is introduced into a suitable, closed packaging arrangement, such as, for example, into a drum, a bag or a cartridge, and can be stored and transported in this packaging.

It is also possible for the packagings of the components C1 and C2 to be connected to one another. Thus, for example, it is possible to introduce component C1 and C2 into one container each of a dual cartridge. For example, these are so-called coaxial cartridges or twin cartridges. Such packagings which contain components C1 and C2 in chambers spatially separated from one another are advantageous in that the two components remain together in an inseparable manner and in such a way that they cannot be lost during storage and during transport and therefore need not first be gathered or brought together for the application of the two-component composition.

The two components C1 and C2 are mixed with one another before or during the application of the two-component composition. The mixing can be effected in various ways.

In particular, the mixing can be effected substantially homogeneously or inhomogeneously. The mixing of the two components is preferably effected via a static mixer or via a dynamic mixer. This results in a mixed or partly mixed two-component composition.

FIGS. 1a to 1f show some examples of such mixing operations.

FIGS. 2a to 2f show examples of mixing apparatuses with which such mixing patterns can be achieved.

In one embodiment, the mixing of the two components C1 and C2 is effected substantially homogeneously.

This can be achieved in particular by the use of dynamic mixers. It is also possible to achieve substantially homogeneous mixing by using static mixers having many mixing elements.

As is known to the person skilled in the art, the term "homogeneously mixed" in the context of pasty adhesives and sealants as are discussed here is not to be understood in the absolute sense. In the usual use, the term means in fact that mixing boundaries are no longer visible to the eye, whereas this is entirely possible, for example, under the microscope. On the basis of experimental discoveries, it may be assumed that the mixing of the two pasty components takes place substantially homogeneously with the use of static mixers of the Sulzer Quadro® type (available from Sulzer Chemtech) having 18 or more static mixer elements.

In a further embodiment, the mixing of the two components C1 and C2 takes place substantially inhomogeneously, for example in the form of laminar or strand-like mixing.

Laminar mixing can be achieved in particular by the use of static mixers, these having a limited number of static mixer elements. For example, a metering adaptor as described in WO 95/24556 A1, the total content of which is hereby included in the disclosure of the present invention, and by means of which the component C2 is mixed with the component C1, can be used for this purpose.

The number of static mixer elements is in particular 6 to 16, preferably 6 to 12.

In one variant, strand-like mixing results by virtue of the fact that one or strands of the component C2 are surrounded by the component C1. This can be effected by application apparatus as described in EP 1 728 840 A1. The total content of this document is hereby included in the disclosure of the present invention. In a further variant, a strand of the components C1 and C2 mixed with one another is surrounded by the component C1. This variant has the advantage that rapid curing takes place in the core of the bead, i.e. where the components C1 and C2 are mixed, whereas the surface of the bead cures substantially only via atmospheric moisture since no component C2 is present there. As a result of this, the open time (limited by the skin formation) of such a bead is longer in contrast to a bead which consists of the mixed components C1 and C2 over the total cross section, so that the advantages of a long open time and rapid curing are combined. One possibility for achieving such sheathing is offered by a static mixer as disclosed in WO 02/32562 A1, and the total content thereof is hereby included in the disclosure of the present invention.

Particularly in the case of moisture-curing polyurethane adhesives having a high modulus of elasticity as component C1—especially in the case of those which contain polyaldimines—it has been found that the composition obtained after the inhomogeneous admixing of the component C2 has extremely good processability and a high final strength. This is in contrast to compositions which result from the analogous use of components C2 according to the prior art, especially components C2 containing N-alkylpyrrolidone. In these cases, the processibility is often insufficient only a short time after the admixing of the component C2, which manifests itself, for example, in that a smear taken from the composition has a gritty aspect. Furthermore, the final strength of the cured composition remains limited. This is possibly due to insufficient incorporation of the constituents present in the component C2 into the polyurethane matrix, the result of which is that the cured composition tears when subjected to force within the former layers of the component C2.

The two-component composition described can be used as adhesive, sealant or coating or covering.

When used as an adhesive, the two-component composition is employed for the adhesive bonding of a substrate S1 and a substrate S2. The adhesive bonding is preferably effected by the process described below.

This process for the adhesive bonding of substrates S1 and S2 comprises the steps
  i) applying a two-component composition described above during the mixing or after the mixing of the two components C1 and C2 to a substrate S1;
  ii) bringing the applied composition into contact with a substrate S2;
or
  i') applying a two-component composition described above during the mixing or after the mixing of the two components C1 and C2 to a substrate S1;
  ii') applying a two-component composition described above during the mixing or after the mixing of the two components C1 and C2 to a substrate S2;
  iii') bringing the composition applied to substrate S1 into contact with the composition applied to substrate S2.

Here, the substrates S1 and S2 are identical or different from one another.

When used as a sealant, the two-component composition is employed for sealing substrates. The sealing is preferably effected by the process described below.

This sealing process comprises the step
  i") applying a two-component composition described above during the mixing or after the mixing of the two components C1 and C2 between a substrate S1 and a substrate S2.

Here, the substrates S1 and S2 are identical or different from one another.

When used as a sealant, the composition is employed as a seal between two substrates S1 and S2. Usually, the sealant is pressed into a joint.

The production of a coating is preferably effected by the process described below.

This process for the production of a coating comprises the step
  i''') applying a two-component composition described above during the mixing or after the mixing of the two components C1 and C2 to a substrate S1.

In these three processes, the mixing of the two components C1 and C2 is effected substantially homogeneously in one embodiment. In another embodiment, the mixing of the two components C1 and C2 is effected substantially inhomogeneously. In particular, the inhomogeneous mixing takes place in such a way that a laminar, strand-like or spiral mixing pattern is formed.

A step for curing by means of atmospheric moisture can optionally follow step ii), iii'), i") or i''').

Suitable substrates S1 or S2 are, for example, inorganic substrates, such as glass, glass ceramic, concrete, mortar, baked brick, brick, gypsum and natural stones, such as granite or marble; metals or alloys, such as aluminium, steel, nonferrous metals, galvanized metals; organic substrates, such as wood, plastics, such as PVC, polycarbonates, PMMA, polyester, epoxy resins; coated substrates, such as powder-coated metals or alloys; and paints and finishes. Substrate S1 and/or S2 is preferably selected from the group consisting of concrete, cement, mortar, baked brick, brick, gypsum, natural stone, asphalt, metal, metal alloy, wood, ceramic, glass, plastic, powder coating, paint and finish.

The substrates can, if required, be pretreated prior to the application of the two-component composition. Such pretreatments comprise in particular physical and/or chemical cleaning processes, for example grinding, sandblasting, brushing or the like, or treatment with cleaners or solvents or the application of an adhesion promoter, of an adhesion promoter solution or of a primer.

Particularly advantageously, the process is used for fitting glass panes in means of transport, in particular automobiles.

An article results from one of the described processes for adhesive bonding or for sealing or for the production of a coating.

The article may be a building or a structure of building construction or civil engineering, industrially produced goods or consumer goods, in particular a window, a household appliance or a means of transport, in particular a vehicle, or an add-on part of a vehicle.

The two-component composition described has major advantages, firstly having an excellent early strength and a high final strength and secondly being capable of being formulated so as to be free of VOC solvents, in particular free of N-alkylpyrrolidones, and hence meeting high standards with regard to ecological and occupational hygiene properties.

BRIEF DESCRIPTION OF THE DRAWINGS

Below, selected working examples of the invention are illustrated in more detail by means of the drawings. Identical elements are provided with the same reference numerals in the various figures. The direction of forces or movements is indicated by arrows.

FIG. 1a shows a strand-like mixing pattern with a strand C2

FIG. 1b shows a strand-like mixing pattern with a plurality of strands C2

FIG. 1c shows a strand-like mixing pattern of a strand comprising C1/C2 surrounded by C1

FIG. 1d shows a laminar mixing pattern

FIG. 1e shows a strand-like mixing pattern with a strand C2

FIG. 1b shows a spiral mixing pattern with a strand C2

FIG. 2a-f show a schematic cross-sectional diagram along the longitudinal axis z through a mixing apparatus FIG. 2a shows a mixing apparatus leading to a mixing pattern according to FIG. 1a)

FIG. 2b shows a mixing apparatus leading to a mixing pattern according to FIG. 1b)

FIG. 2c shows a mixing apparatus leading to a mixing pattern according to FIG. 1c)

FIG. 2d shows a mixing apparatus leading to a mixing pattern according to FIG. 1d)

FIG. 2f shows a mixing apparatus leading to a mixing pattern according to FIG. 1f)

FIG. 2f' shows a detail of the end piece 14

Only the elements essential to the direct understanding of the invention are shown. For example, the storage containers and details of the feeding of the components C1 and C2 are not shown.

Figure 1:
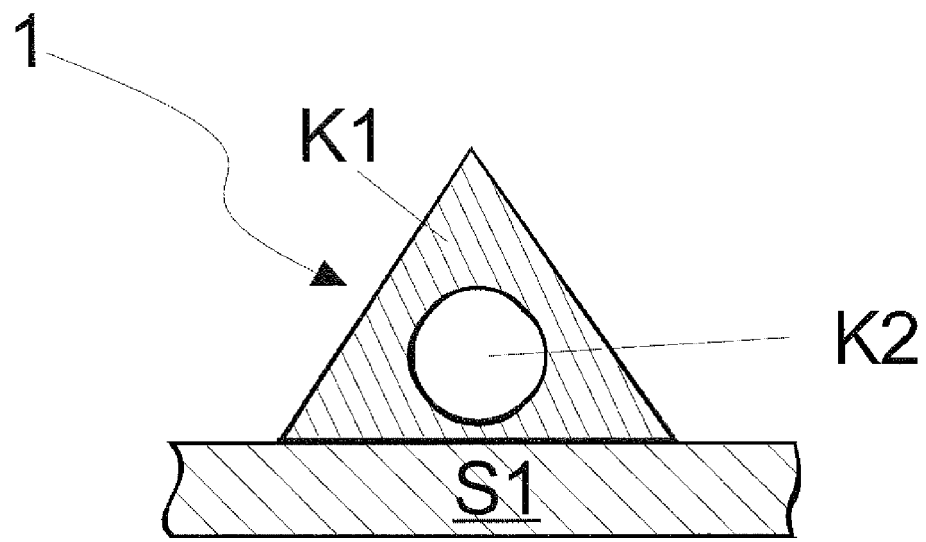
FIG. 1a-d show a schematic cross-sectional diagram through a triangular bead 1, transversely to the bead direction
FIG. 1e-f show a schematic cross-sectional diagram through a triangular bead 1 in the bead direction
Figure 1:
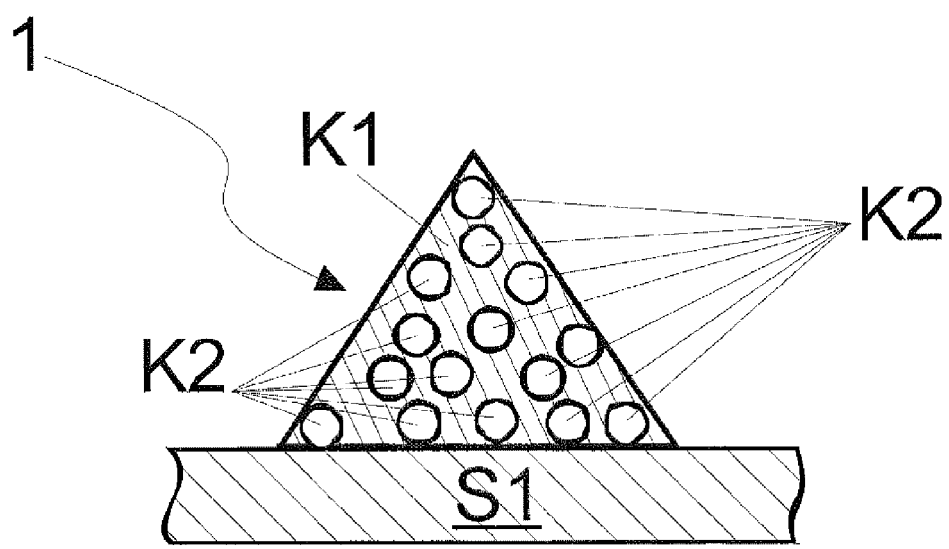
Figure 1:
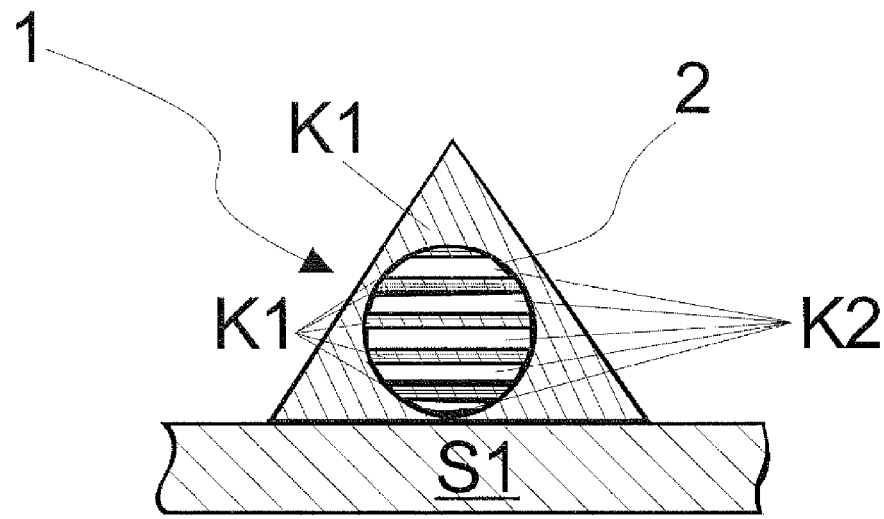
Figure 1:
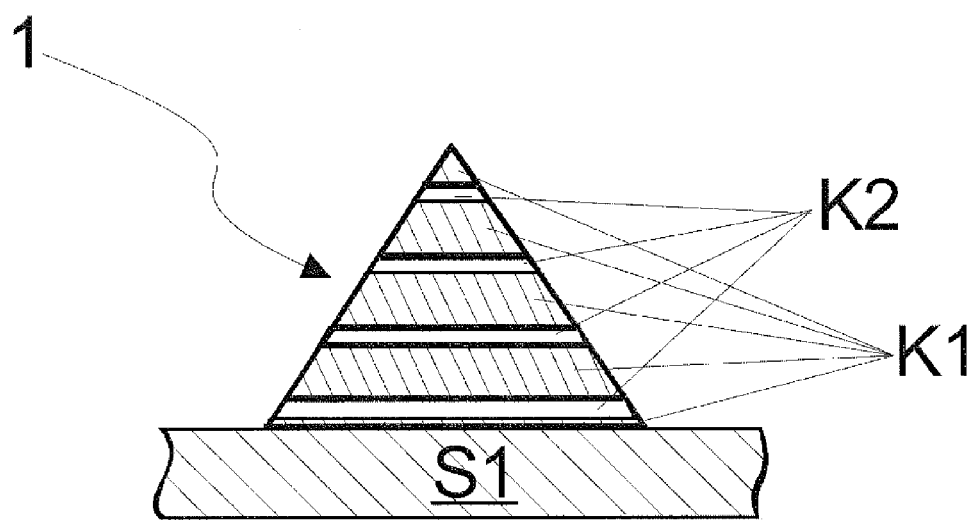
Figure 1:
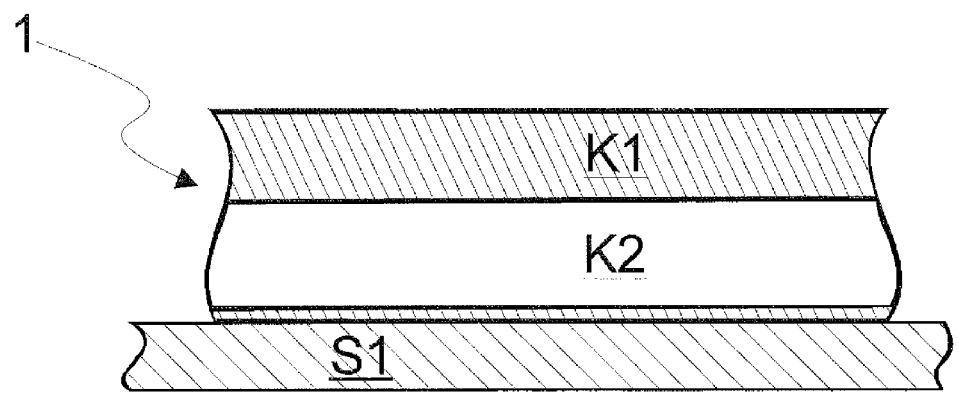
Figure 1:
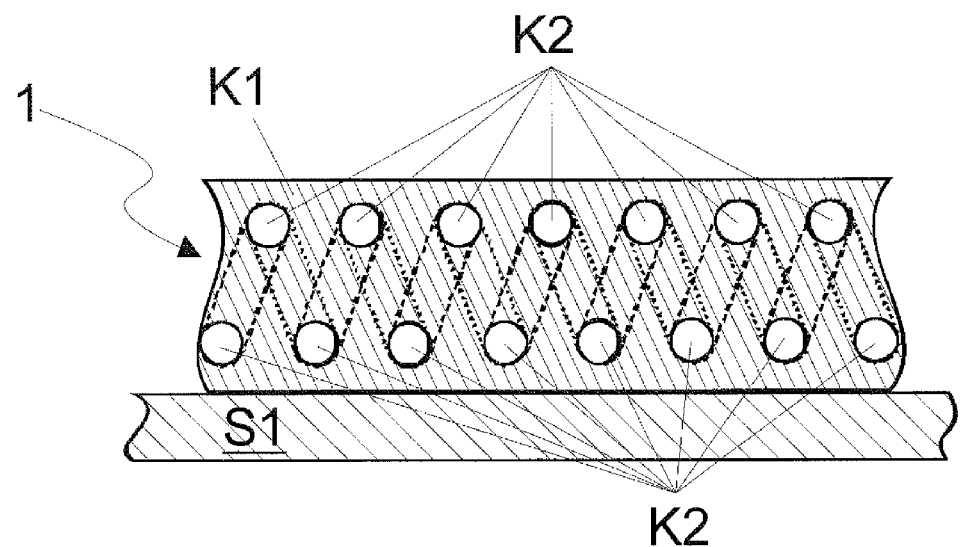

FIG. 1a is a schematic diagram of a cross section through a triangular bead 1, transversely to the bead direction, after partial mixing of components C1 and C2 of a two-component composition, which was applied to a substrate S. In this example, the partial mixing is effected in such a way that a strand-like mixing pattern results, in which a strand of the component C2 is surrounded by component C1.

Figure 2A:
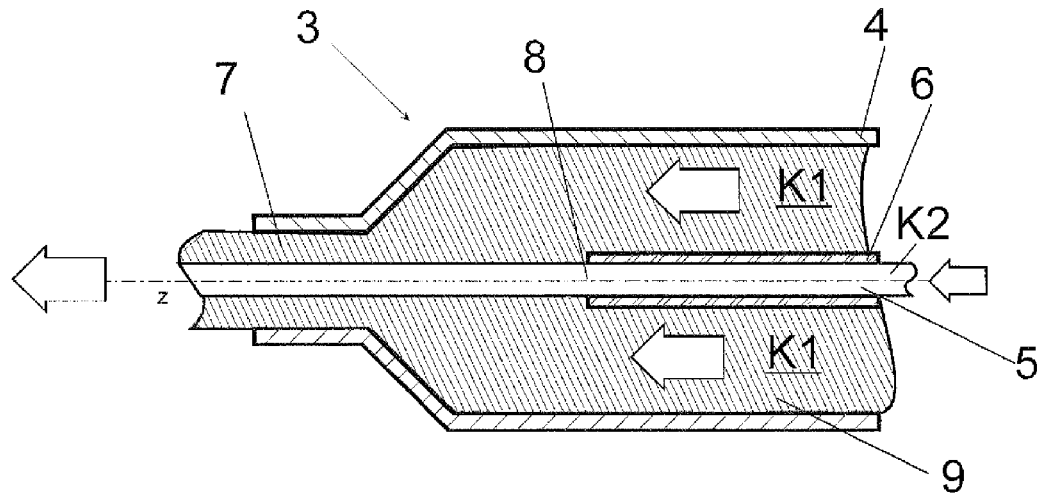

Such a mixing pattern can be achieved, for example, by a mixing apparatus as shown schematically in FIG. 2a.

FIG. 1b is a schematic diagram of a cross section through a triangular bead 1, transversely to the bead direction, after partial mixing of components C1 and C2 of a two-component composition, which was applied to a substrate S1. In this example, the partial mixing is effected so that a strand-like mixing pattern results, in which a plurality of strands of component C2 are surrounded by C1.

Figure 2B:
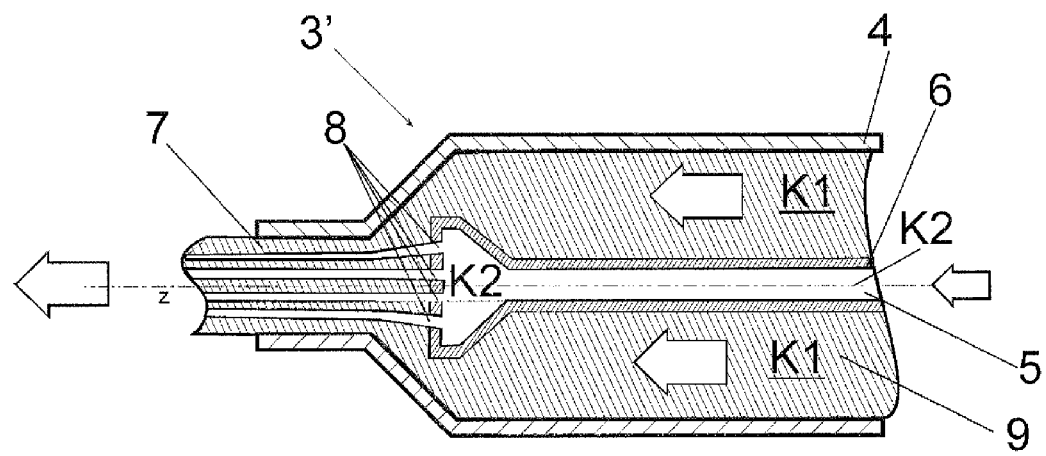

Such a mixing pattern can be achieved, for example, by a mixing apparatus as shown schematically in FIG. 2b.

FIG. 1c is a schematic diagram of a cross section through a triangular bead 1, transversely to the bead direction, after partial mixing of components C1 and C2 of a two-component composition, which was applied to a substrate S1. In this example, the partial mixing is effected by surrounding a mixing region 2, where the components C1 and C2 are completely or partly mixed with one another, by the unmixed component C1. In the embodiment shown here, the mixing in the mixing region 2 is laminar.

Figure 2C:
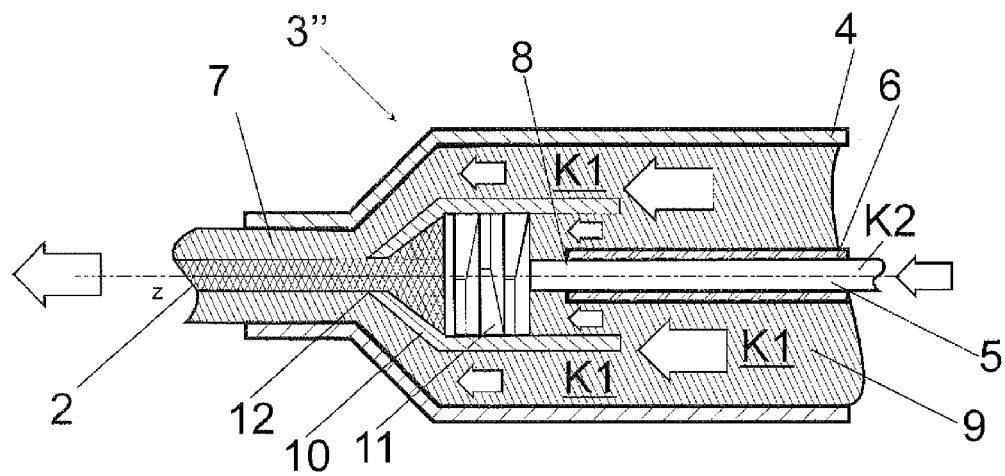

Such a mixing pattern can be achieved, for example, by a mixing apparatus as shown schematically in FIG. 2c.

FIG. 1d is a schematic diagram of a cross section through a triangular bead 1, transversely to the bead direction, after partial mixing of components C1 and C2 of a two-component composition, which was applied to a substrate S1. In this example, partial mixing is effected in a laminar manner.

Figure 2D:
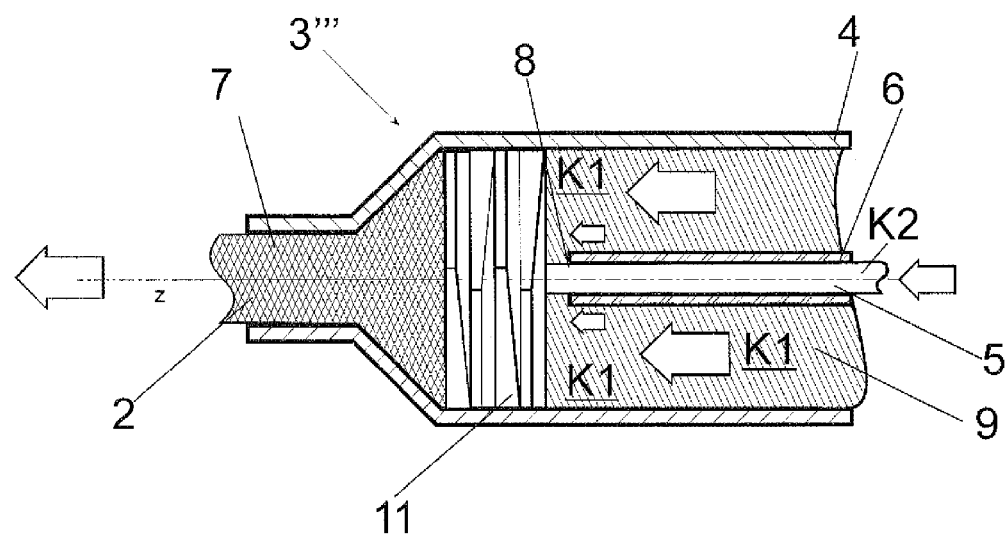

Such a mixing pattern can be achieved, for example, by a mixing apparatus as shown schematically in FIG. 2d.

FIG. 1e is a schematic diagram of a cross section through a triangular bead 1 in the bead direction after partial mixing of components C1 and C2 of a two-component composition, which was applied to a substrate S1. In this example, the partial mixing takes place in the form of a strand C2 which is surrounded by C1 and which is oriented colinearly with the bead so that a strand-like mixing pattern results.

Such a mixing pattern can be achieved, for example, by a mixing apparatus as shown schematically in FIG. 2a.

FIG. 1f is a schematic diagram of a cross section through a triangular bead 1 in the bead direction after partial mixing of components C1 and C2 of a two-component composition, which was applied to a substrate S1. In this example, the partial mixing takes place in the form of a strand C2 which is surrounded by C1 and which is oriented spirally in the adhesive bead so that a spiral mixing pattern results.

Such a mixing pattern can be achieved, for example, by a mixing apparatus as shown schematically in FIG. 2f.

FIG. 2a schematically shows a cross section along the longitudinal axis z through a mixing apparatus 3 which leads to a strand-like mixing pattern, as shown in FIG. 1a. The mixing apparatus 3 has a feed pipe 4 for the component C1, which bounds an interior 9 in a tubular manner, in which interior the component C1 is fed. A feed pipe 6 for component C2 projects into this interior 9. On application or mixing, the component C1 is forced through the feed pipe 4 and the component C2 through the feed pipe 6. After passing through the outlet opening 8 of the feed pipe for the component C2, the two components C1 and C2 are in contact with one another downstream, and partial mixing of the two components takes place. On emergence from the outlet opening 7 of the mixing apparatus, a strand-like mixing pattern is found in which the component C2 is surrounded by the component C1.

FIG. 2b schematically shows a cross section along the longitudinal axis z through a mixing apparatus 3' which leads to a strand-like mixing pattern, as shown in FIG. 1b. The mixing apparatus 3' is a variant of the mixing apparatus 3 which was discussed beforehand in FIG. 2a. In this variant, the feed pipe 6 projecting into the interior 9 and intended for the component C2 has a plurality of outlet openings 8 of the feed pipe 6. As a result, a mixing pattern as shown in FIG. 1b, in which a plurality of strands of the component C2 are surround by the component C1, results on emergence from the outlet opening 7 of the mixing apparatus.

FIG. 2c schematically shows a cross section along the longitudinal axis z through a mixing apparatus 3'' which leads to a mixing pattern as shown in FIG. 1c. The mixing apparatus 3'' has a feed pipe 4 for the component C1, which bounds an interior 9 in a tubular manner, in which interior the component C1 is fed. A feed pipe 6 for the component C2 projects into this interior 9. On application or mixing, the component C1 is forced through the feed pipe 4 and the component C2 through the feed pipe 6. After passing through the outlet opening 8 of the feed pipe for component C2, the two components C1 and C2 are in contact with one another downstream and are mixed with one another by a plurality of static mixer elements 11 which are arranged in a static mixer 10. The mixed stream is folded by each static mixer element 11, and a laminar mixing pattern forms in the mixing region 2 after emergence from the outlet opening 12 of the static mixer. Because the static mixer 10 is arranged centrally in the feed pipe for the component C1, a part of the component C1 flows around the static mixer in a sheath-like manner and, after passing through the outlet opening 12 of the static mixer 10, surrounds downstream the strand 2 mixed via the static mixer and comprising component C1 and C2. This gives rise to a mixing pattern as shown in FIG. 1c on emergence from the outlet opening 7 of the mixing apparatus.

FIG. 2d schematically shows a cross section along the longitudinal axis z through a mixing apparatus 3''' which leads to a mixing pattern as shown in FIG. 1d. The mixing apparatus 3''' is a variant of the mixing apparatus 3'' as discussed in FIG. 2c. In contrast to the embodiment of FIG. 2c, here the entire stream of the component C1 is mixed with the component C2 over a plurality of static mixer elements 11. This gives rise to a mixing pattern as shown in FIG. 1d on emergence from the outlet opening 7 of the mixing apparatus. The same result is in principle also obtained if a static mixer according to the prior art is attached to the outlet opening 7 of a mixing apparatus 3 as shown in FIG. 2a.

FIG. 2f schematically shows a cross section along the longitudinal axis z through a mixing apparatus 3''' which leads to a mixing pattern having the cross section according to FIG. 1a or FIG. 1f. The mixing apparatus 3''' has a feed pipe 4 for the component C1 which bounds an interior 9 in an annular manner, in which interior the component C1 is fed. A feed pipe 6 for the component C2 projects into this interior 9 of width $d_B$. In this embodiment, this feed pipe is designed to be rotatable as part of a rotating element 13 of width $d_T$. The feed pipe ends at the side of the rotating element 13. In the embodiment shown here, the end piece 14, which is shown in detail in FIG. 2f', is the end of the feed pipe 6 of the component C2. The end piece 14 has a bore 15 which thus connects feed pipe to the outlet opening 8. The end piece is connected to the remainder of the feed pipe 6 via a thread 16 and is fixed by means of locknut 17. As a result of rotation of the rotating element 13, and hence of the feed pipe 6, the outlet opening 8 executes a circular movement inside the interior 9. On application or on mixing, the components C1 and C2 are simultaneously transported, and a spiral strand of component C2, which is surrounded by component C1, is formed. This gives rise to a mixing pattern as shown in FIG. 1a or in FIG. 1f on emergence from the outlet opening 7 of the mixing apparatus.

It is clear to the person skilled in the art that the embodiments shown here are merely illustrative and should by no means be considered as limiting. Of course, different variants are conceivable. In particular, the mixing of the two components can be optimized by the use of a larger number of static mixer elements 11 or by the use of dynamic mixing elements or dynamic mixers, and quasi-homogeneous or homogeneous mixtures of the two components can be obtained.

LIST OF REFERENCE NUMBERS 1 bead
2 mixing region
3, 3', 3'', 3''', 3'''' mixing apparatus
4 outer wall of mixer
5 interior of the feed pipe for component C2
6 feed pipe for component C2
7 outlet opening of the mixing apparatus
8 outlet opening of the feed pipe for component C2
9 interior of the feed pipe for component C1
10 static mixer
11 static mixer element
12 outlet opening of the static mixer
13 rotating element
14 end piece of the feed pipe of component C2
15 bore through end piece 14
16 thread in end piece 14
17 locknut

EXAMPLES

Description of the Methods of Measurement

Infrared spectra were measured on an FT-IR apparatus 1600 from Perkin-Elmer (horizontal ATR measuring unit with ZnSe crystal). The samples were applied in undiluted form as films. The absorption bands are stated in wave numbers ($cm^{-1}$) (measuring window: 4000-650 $cm^{-1}$).

The amine content of the dialdimines prepared, the content of protected amino groups in the form of aldimino groups, was determined titrimetrically (with 0.1N $HClO_4$ in glacial acetic acid, against crystal violet) and is stated in mmol N/g.

a) Preparation of Dialdimines of the Formula (IV)

Polyaldimine A1

55.0 g (0.19 mol) of distilled 2,2-dimethyl-3-lauroyloxypropanal were initially introduced under a nitrogen atmosphere into a round-bottomed flask. 13.7 g (0.18 mol of N) of 3,6-dioxaoctane-1,8-diamine (Jeffamine® XTJ-504, Huntsman; amine content 13.34 mmol N/g) were slowly added from a dropping funnel with vigorous stirring, the mixture heating up. Thereafter, the volatile constituents were removed in vacuo (10 mbar, 80° C.). Yield: 65.1 g of a clear, colourless oil having an amine content of 2.81 mmol N/g.

IR: 2954, 2920, 2852, 1736 (C=O), 1668 (C=N), 1466, 1419, 1394, 1373, 1366, 1351, 1340sh, 1298sh, 1282sh, 1248, 1232, 1156, 1114, 1057, 1020, 998, 932, 917sh, 876sh, 837, 791, 767, 722.

Dialdimine A2

74.3 g (0.26 mol) of distilled 2,2-dimethyl-3-lauroyloxypropanal were initially introduced under a nitrogen atmosphere into a round-bottomed flask. 30.0 g (0.25 mol of N) of polyetherdiamine (polyoxypropylenediamine having an average molecular weight of about 240 g/mol; Jeffamine® D-230, Huntsman; amine content 8.32 mmol N/g) were slowly added from a dropping funnel with vigorous stirring, the mixture heating up and becoming increasingly cloudy. Thereafter, the volatile constituents were removed in vacuo (10 mbar, 80° C.). Yield: 99.3 g of a clear, pale yellow oil having an amine content of 2.53 mmol N/g.

b) Preparation of Polyurethane Emulsions

Emulsion E1

An emulsion containing a dialdimine of the formula (I) having an average molecular weight of about 11 000 was prepared as follows: 72.7 g of polyurethanepolymer P1 the preparation of which is described below, 17.3 g of dialdimine A1, 0.3 g of salicylic acid solution (5% by weight in dioctyl adipate) and 90.0 g of polyethylene glycol dibutyl ether (polyglycol BB 300, Clariant; average molecular weight 300) were homogeneously mixed in a vacuum mixer and heated to 60° C. 76.2 g of water were stirred in and the mixture was stirred at 60° C. for 20 minutes. A milky white, low-viscosity emulsion having a water content of 29.5% by weight was obtained.

The polyurethanepolymer P1 was prepared as follows:

4000 g of polyoxypropylenediol (Acclaim® 4200 N, Bayer; OH number 28.5 mg KOH/g) and 520 g of 4,4'-methylenediphenyl diisocyanate (MDI; Desmodur® 44 MC L, Bayer) were reacted at 80° C. to give a polyurethanepolymer terminated with isocyanate groups and having a titrimetrically determined content of 1.86% by weight of free isocyanate groups.

Emulsion E2

An emulsion containing an organic polymer having ionic groups and having an average molecular weight of about 20 000 was prepared by a known process by polyaddition of isophorone diisocyanate (IPDI; Vestanat® IPDI, Degussa) with Polyol Caradol® ED56-11 (Shell), aminoethylethanolamine and 2,2-bis(hydroxymethyl)propionic acid in N-methylpyrrolidone (NMP), subsequent neutralization with triethylamine and addition of water to a water content of 29.5% by weight. A milky emulsion was obtained.

Emulsion E3

An attempt was made to prepare an emulsion analogous to the emulsion E2 but NMP-free and containing an organic polymer having ionic groups, by replacing the N-methylpyrrolidone in the procedure described for the emulsion E2 by diethylene glycol dimethyl ether (Clariant), which is a customary NMP substitute. On addition of the aminoethylethanolamine, however, the polymer gelled and could no longer be emulsified.

c) Preparation of Accelerator Components C2

Accelerator Component AC1

85 g of the emulsion E1 were initially introduced into a vacuum mixer and mixed with 1 g of technical-grade sodium dodecylbenzenesulphonate (Rhodacal® DS-10, Rhodia), 1 g of sodium tallate (Dresinate® TX, Eastman), 0.5 g of triethylamine, 7.5 g of polyethylene glycol dibutyl ether (Polyglycol BB 300, Clariant; average molecular weight 300), 5 g of hydrophilic pyrogenic silica (Aerosil® 200, Degussa) and 5 g of hydrophobic pyrogenic silica (Aerosil®R972, Degussa) to give a finely creamy paste.

Accelerator Component AC2

85 g of the emulsion E2 were initially introduced into a vacuum mixer and mixed with 10 g of hydrophilic pyrogenic silica (Aerosil® 200, Degussa) and 5 g of chalk (Omya® 5 GU, Omya) to give a finely creamy paste.

Accelerator Component AC3

83.5 g of dialdimine A2, 6.2 g of water, 10.0 g of hydrophilic pyrogenic silica (Aerosil® 200, Degussa) and 0.3 g of salicylic acid solution (5% by weight in dioctyl adipate) were mixed in a vacuum mixer to give a homogeneous paste.

d) Preparation of a One-component Polyurethane Composition (Corresponding to a Component C1)

Composition CO1

180 g of polyurethanepolymer P2, the preparation of which is described below, 97 g of diisodecyl phthalate (DIDP; Palatinol® Z, BASF), 18 g of hydrophobic pyrogenic silica (Aerosil® R972, Degussa), 54 g of carbon black, 90 g of calcined kaolin, 1.3 g of 3-glycidyloxypropyltrimethoxysilane (Silquest® A-187, GE Advanced Materials), 0.9 g of Desmodur® CD (Bayer) and 9 g of a solution of 10% by weight of 2,2'-Dimorpholinodiethyl ether (DABCO® DMDEE Catalyst, Air Products) and 2% by weight of dibutyltin dilaurate in DIDP were mixed in a vacuum mixer at 40° C. to give a homogeneous paste, the mixture was introduced into internally coated aluminium cartridges and these were closed air-tight. The composition had a content of 0.20 mmol NCO/g of isocyanate groups and a density of 1.26 g/cm$^3$.

The polyurethanepolymer P2 was prepared as follows:

1300 g of polyoxypropylenediol (Acclaim® 4200 N, Bayer; OH number 28.5 mg KOH/g), 2600 g of polyoxypropylenepolyoxyethylenetriol (Caradol® MD34-02, Shell; OH number 35.0 mg KOH/g), 600 g of 4,4'-methylenediphenyl diisocyanate (MDI; Desmodur® 44 MC L, Bayer) and 500 g of diisodecyl phthalate (DIDP; Palatinol® Z, BASF) were reacted at 80° C. to give a polyurethane polymer terminated with isocyanate groups and having a content of 2.05% by weight of free isocyanate groups.

e) Preparation and Testing of Two-component Polyurethane Adhesives (Consisting of Components C1 and C2)

Example 1 and Comparative Examples 2 and 3

For each example, the respective components C1 and C2 according to Table 1 were substantially homogeneously mixed in the stated volume ratio and investigated with regard to their curing behaviour.

The mixing of the two components C1 and C2 was effected continuously during application, by applying the polyurethane adhesive by means of a two-component gun with attached static mixer of the Sulzer Quadro® type (available from Sulzer Chemtech) with 24 mixing elements.

For investigation of the curing behaviour, the two-component polyurethane adhesives were tested firstly for early strength and secondly for sectility after application.

For testing the early strength, the tensile shear strength was measured by means of the following method: for each measurement, in each case 2 small glass plates of 6 mm thickness, 25 mm width and 75 mm length (float glass; from Rocholl, Schönbrunn, Germany) were pretreated with Sika® activator (available from Sika Schweiz AG). After drying in the air for 10 minutes, the small plates were arranged with the aid of a suitable PTFE mould with a vertical spacing of 4 mm relative to one another so that they overlapped by 12 mm at the top ends. The overlap region between the small plates was filled with adhesive, the latter coming to rest on the activated sides of the small plates. The small plates adhesively bonded to one another in this manner were stored at 23° C. and 50% relative humidity and pulled apart after 2 or 4 or 24 hours with the aid of a tensile tester (Zwick) at a constant transverse yoke speed of 20 mm/min according to DIN EN 1465 until fracture occurred, and the breaking force in MPa (N/mm$^2$) was measured. The stated values are mean values of three measurements.

For determining the sectility, the adhesive was applied in the form of a triangular bead of about 1 cm base area to an LDPE film, and the bead was left at 23° C. and 50% relative humidity for 2 hours and then cut through centrally in the longitudinal direction with a cutter. The adhesive was rated as being sectile when the blade of the cutter remained unsoiled on cutting through the bead, i.e. the adhesive was crosslinked to such an extent that it left behind no residues of uncrosslinked material on cutting.

The results of the tests carried out are shown in Table 1.

TABLE 1

Composition of the two-component polyurethane adhesives of Example 1 and of Comparative Examples 2 and 3.

| Example | 1 | 2 (comparison) | 3 (comparison) |
|---|---|---|---|
| Component C1 | CO1 | CO1 | CO1 |
| Component C2 | AC1 | AC2 | AC3 |
| Volume ratio C1/C2 | 98/2 | 98/2 | 95/5 |
| Early strength after 2 h (MPa) | >5 | >5 | 0.3 |
| Early strength after 4 h (MPa) | >5 | >5 | 0.9 |
| Early strength after 24 h (MPa) | >5 | >5 | 3.6 |
| Sectility after 2 h | yes | yes | (yes)[a] |
| NMP-containing | no | yes | no |

[a] very soft.

Example 4 and Comparative Examples 5 and 6

For each example, the respective components C1 and C2 according to Table 2 were mixed in a substantially laminar manner in the stated volume ratio and investigated with regard to the curing behaviour.

The mixing of the two components C1 and C2 was effected continuously during application, by applying the polyurethane adhesive by means of a two-component gun with attached static mixer with 10 mixing elements (type TAH-510, from GLT, Germany).

For investigating the curing behaviour, the two-component polyurethane adhesives were tested firstly for early strength and secondly for sectility after application, as described in Example 1. The results of the tests carried out are shown in Table 2.

TABLE 2

Composition of the two-component polyurethane adhesives of Example 4 and of Comparative Examples 5 and 6.

| Example | 4 | 5 (comparison) | 6 (comparison) |
|---|---|---|---|
| Component C1 | CO1 | CO1 | CO1 |
| Component C2 | AC1 | AC2 | AC3 |
| Volume ratio C1/C2 | 98/2 | 98/2 | 95/5 |
| Early strength after 2 h (MPa) | 1.6 | >5 | n.m.[a] |
| Early strength after 4 h (MPa) | 1.9 | >5 | 0.7 |
| Early strength after 24 h (MPa) | 2.7 | >5 | 2.0 |
| Sectility after 2 h | yes | yes | no |
| NMP-containing | no | yes | no |

[a] not measurable.

The comparison of Example 1 according to the invention with Comparative Example 2, which is based on an NMP-containing accelerator component AC2 corresponding to the prior art, shows that excellent early strength is obtained in the case of substantially homogeneous mixing. An NMP-free accelerator component corresponding to the accelerator component AC2 could not be prepared since gelling occurred even during the preparation of the corresponding emulsion E3 (as already described above).

Furthermore, the results from Tables 1 and 2 show that Examples 1 and 4 according to the invention have a greatly improved early strength and a better sectility compared with Comparative Examples 3 and 6, which are based on accelerator component AC3 corresponding to the prior art.

The invention claimed is:
1. A two-component composition consisting of two components C1 and C2,
the component C1 containing at least one polymer having isocyanate groups; and
the component C2 containing an aldimine-containing emulsion comprising:
a) at least one dialdimine of the formula (I),

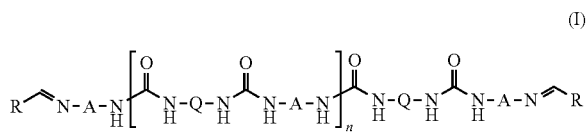

in which R represents the radical of an aldehyde ALD after removal of an aldehyde group;
A represents the radical of a diamine DA having two primary aliphatic amino groups after removal of the two primary aliphatic amino groups;
Q represents the radical of a diisocyanate DI after removal of both isocyanate groups;
n represents 0 or represents an integer from 1 to 15; and
in which A and R have no groups which are reactive with isocyanate groups in the absence of water,
wherein the dialdimine of formula (I) is prepared by a process comprising the step of reacting a diisocyanate DI with a dialdimine of the formula (IV), in the presence of water,

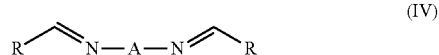

the diisocyanate DI and the dialdimine of the formula (IV) being reacted in the molar ratio of
[diisocyanate DI]/[dialdimine of the formula (IV)] of <1, and
the amount of water being chosen so that the molar ratio [water]/[diisocyanate DI] is ≥2; and
b) water,
wherein the two-component composition consisting of two components C1 and C2 is an emulsion when mixed.
2. A mixed or partly mixed two-component composition, wherein the component C1 and the component C2 of the two-component composition according to claim 1 are mixed substantially homogeneously or inhomogeneously with one another, the mixing of the two components being effected via a static mixer or a dynamic mixer.
3. The two-component composition according to claim 1, wherein the component C2 further comprises a surfactant.
4. The two-component composition according to claim 3, wherein the surfactant is an anionic surfactant.
5. The two-component composition according to claim 1, wherein in the step of reacting a diisocyanate DI with a dialdimine of the formula (IV), the amount of water being chosen so that the molar ratio:
[water]/[diisocyanate DI] is ≥10.
6. A method for preparing the two-component composition of claim 1, comprising:
adding water to the at least one dialdimine of the formula (I) to form the aldimine-containing emulsion.
7. A two-component composition consisting of two components C1 and C2,
the component C1 containing at least one polymer having isocyanate groups; and
the component C2 containing an aldimine-containing emulsion comprising:

a) at least one dialdimine of the formula (I),

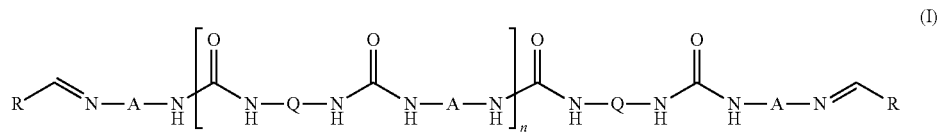

in which R represents the radical of an aldehyde ALD after removal of an aldehyde group;
A represents the radical of a diamine DA having two primary aliphatic amino groups after removal of the two primary aliphatic amino groups;
Q represents the radical of a diisocyanate DI after removal of both isocyanate groups;
n represents 0 or represents an integer from 1 to 15; and
in which A and R have no groups which are reactive with isocyanate groups in the absence of water, wherein the dialdimine of formula (I) is prepared by a process comprising the step of reacting a diisocyanate DI with a dialdimine of the formula (IV), in the presence of water,

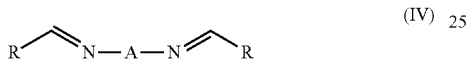

the diisocyanate DI and the dialdimine of the formula (IV) being reacted in the molar ratio of
[diisocyanate DI]/[dialdimine of the formula (IV)] of <1, and
the amount of water being chosen so that the molar ratio [water]/[diisocyanate DI] is ≥2;
b) water; and
c) at least one surfactant.

* * * * *